US008475784B2

(12) United States Patent
Hjorth et al.

(10) Patent No.: US 8,475,784 B2
(45) Date of Patent: *Jul. 2, 2013

(54) IL-21 VARIANTS

(75) Inventors: Siv Annegrethe Hjorth, Virum (DK);
Kent Bondensgaard, Vaerlose (DK);
Dennis Madsen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 152 days.

This patent is subject to a terminal disclaimer.

(21) Appl. No.: 12/447,047

(22) PCT Filed: Oct. 26, 2007

(86) PCT No.: PCT/EP2007/061543
§ 371 (c)(1),
(2), (4) Date: Dec. 22, 2009

(87) PCT Pub. No.: WO2008/049920
PCT Pub. Date: May 2, 2008

(65) Prior Publication Data
US 2010/0143292 A1 Jun. 10, 2010

(30) Foreign Application Priority Data
Oct. 26, 2006 (EP) .................................. 06123040

(51) Int. Cl.
*A61K 38/20* (2006.01)
(52) U.S. Cl.
USPC ........................ 424/85.2; 530/351; 435/69.52
(58) Field of Classification Search
None
See application file for complete search history.

(56) References Cited

U.S. PATENT DOCUMENTS

| | | | |
|---|---|---|---|
| 4,902,502 A | 2/1990 | Nitecki et al. | |
| 5,494,662 A | 2/1996 | Kohji et al. | |
| 5,643,756 A | 7/1997 | Kayman et al. | |
| 5,739,208 A | 4/1998 | Harris | |
| 6,307,024 B1 * | 10/2001 | Novak et al. ................... | 530/351 |
| 6,423,685 B1 | 7/2002 | Drummond et al. | |
| 6,455,043 B1 | 9/2002 | Grillo-Lopez | |
| 6,929,932 B2 | 8/2005 | Presnell et al. | |
| 7,148,220 B2 | 12/2006 | Vite et al. | |
| 7,186,805 B2 | 3/2007 | Presnell et al. | |
| 7,250,274 B2 | 7/2007 | Chan et al. | |
| 7,276,478 B2 | 10/2007 | Sivakumar et al. | |
| 7,528,104 B2 | 5/2009 | Holmes et al. | |
| 8,034,326 B2 * | 10/2011 | Hjorth et al. .................. | 424/85.2 |
| 2003/0003545 A1 | 1/2003 | Ebner et al. | |
| 2003/0108549 A1 | 6/2003 | Carter et al. | |
| 2003/0134390 A1 | 7/2003 | Presnell et al. | |
| 2003/0186387 A1 | 10/2003 | Ebner et al. | |
| 2004/0009150 A1 | 1/2004 | Nelson et al. | |
| 2004/0228833 A1 | 11/2004 | Costantino et al. | |
| 2006/0024268 A1 | 2/2006 | Kasaian et al. | |
| 2007/0073506 A1 | 3/2007 | Boskovic | |

FOREIGN PATENT DOCUMENTS

| | | |
|---|---|---|
| JP | 2001-510033 | 7/2001 |
| WO | WO 93/24138 A1 | 12/1993 |
| WO | WO 94/12219 | 6/1994 |
| WO | WO 96/40248 A1 | 12/1996 |
| WO | WO 96/41813 | 12/1996 |
| WO | WO 99/03887 | 1/1999 |
| WO | WO 00/53761 | 9/2000 |
| WO | WO 01/79271 | 6/2001 |
| WO | WO 01/46420 | 10/2001 |
| WO | WO 02/053761 | 7/2002 |
| WO | WO 03/040313 | 3/2003 |
| WO | WO 03/028630 | 4/2003 |
| WO | WO 03/044056 | 5/2003 |
| WO | WO 03/082212 | 10/2003 |
| WO | WO 03/087320 | 10/2003 |
| WO | WO 03/103589 | 12/2003 |
| WO | WO 2004/055168 | 7/2004 |
| WO | WO 2004/112703 A | 12/2004 |
| WO | WO 2005/035565 | 4/2005 |
| WO | WO 2005/037306 | 4/2005 |
| WO | WO 2005/052139 | 6/2005 |
| WO | WO 2005/053761 | 6/2005 |
| WO | WO 2005/113001 | 12/2005 |
| WO | WO 2006/111524 A | 10/2006 |
| WO | WO 2006/135385 | 12/2006 |
| WO | WO 2008/074863 | 6/2008 |

OTHER PUBLICATIONS

Blohm et al., "Lack of Effector Cell Function and Altered Tetramer Binding of Tumor-Infiltrating Lymphocytes", J. Immunol., Sep. 2002, 169(10), 5522-5530.
Bondensgaard et al., "The Existence of Multiple Conformers of Interluekin-21 Directs Engineering of a Superpotent Analogue", The Journal of Biological Chemistry, Aug. 10, 2007, 282(32), 23326-23336.
Collins, "IL-21 and IL-21 Receptor: A New Cytokine Pathway Modulates Innate and Adaptive Immunity", Immunol. Res., 2003, 28(2), 131-140.
Communication From the EP Examining Division for EP Application No. 04762905.0, Dated Jun. 3, 2009, 8 pages.
Delgado et al., "The Uses and Properties of PED-Linked Proteins", Crit. Rev. In Thera. Drug Carr Systems, 1992, 9(3-4), 249-304.
Dunn et al., "Cancer Immunoediting: From Immunosurveillance to Tumor Escape", Nat. Immunol., Nov. 2002, 3(11), 991-998.
Genmab, "Genmab Present New Humax-CD20 and Humax-EFGr Pre-Clinical Data", Genmab News Release, Feb. 7, 2003, 1-3.
International Patent Application No. PCT/EP2007/064326: International Preliminary Report, Dated Jun. 24, 2009, 6 pages.
Kataki et al., "Tumor Infiltrating Lymphocytes and Macrophages Have a Potential Dual Role in Lung Cancer by Supporting Both Host-Defense and Tumor Progression", J. Lab. Clin. Med., Nov. 2002, 140(5), 320-328.

(Continued)

Primary Examiner — Dong Jiang
(74) Attorney, Agent, or Firm — Nelson Mullins Riley & Scarborough LLP; Jane E. Remillard, Esq.; Jeanne M. DiGiorgio

(57) ABSTRACT

IL-21 variants are provided wherein amino acids have been deleted in the region consisting of amino acid residues no. 65 to 98.

6 Claims, 3 Drawing Sheets

OTHER PUBLICATIONS

Figure 1:
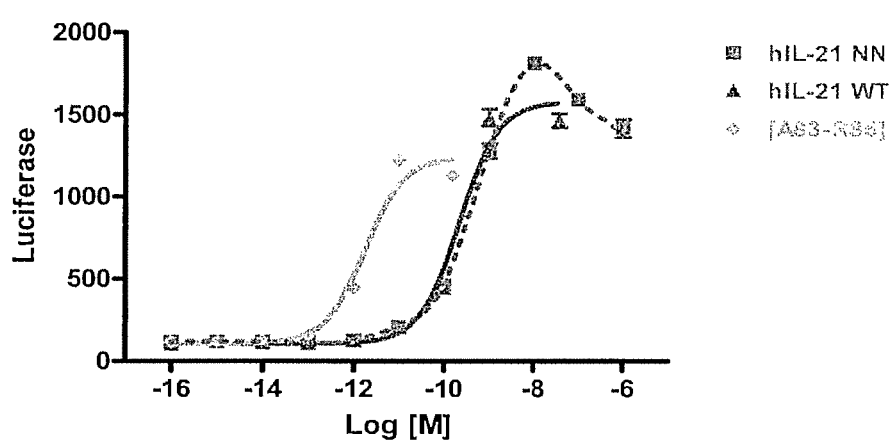

Katre, "The Conjugation of Proteins With Polyethylene Glycol and Other Polymers", Adv. Drug Deliv. Rev., Jan.-Apr. 1993, 10(1), 91-114.

Kelso, "Cytokines: Principles and Prospects", Immunology and Cell Biology, Mar. 1998, 76, 300-317.

Khong et al., "Natural Selection of Tumor Variants in the Generation of "Tumor Escape" Phenotypes", Nat. Immunol. Nov. 2002, 3(11), 999-1005.

Kinstler el al., "Mono-N-Terminal Poly(ethylene glycol)-Protein Conjugates", Adv. Drug Deliv. Rev., Jun. 17, 2002, 54(4), 477-485.

Knauf et al., "Relationship of Effective Molecular Size to Systemic Clearance in Rats of Recombinant Interleukin-2 Chemically Modified With Water-Soluble Polymers", J. Biol. Chem., Oct. 15, 1988, 263(29), 15064-15070.

Leonard et al., "Interleukin-21: A Modulator of Lymphoid Proliferation, Apoptosis and Differentiation", Nature Reviews, Immunology, Sep. 2005, 5(9), 688-698.

Mehta et al., "Biology of IL-21 and the IL-21 Receptor", Immunological Reviews, Munksgaard, Dec. 2004, 202, 84-95.

Parrish-Novak et al., "Interleukin 21 and Its Receptor are Involved in NK Cell Expansion and Regulation of Lymphocyte Function", Nature, Nov. 2, 2000, 408(6808), 57-63.

Response to the Jun. 3, 2009 Communication From the EP Examining Division for Ep Application No. 04762905.0, Dated Jan. 6, 2010, 6 pages.

Sivakumar et al., "Interleukin-21 is a T-hepler Cytokine That Regulates Humoral Immunity and Cell-Mediated Anti-Tumor Responses", Immunology, Blackwell Publishing, Oxford, GB, Mar. 2004, 112, 177-182.

Smyth et al., "Cytokines in Cancer Immunity and Immunotherapy", Immunological Reviews, 2004, 202, 275-293.

Wei-Chiang, "Oral Peptide and Protein Delivery: Unfulfilled Promises?", Drug Discovery Today, Jul. 15, 2003, 8(14), 607-608.

Zalipsky, "Chemistry of Polyethylene Glycol Conjugates with biologically active molecules", Adv. Drug Deliv. Rev., Sep. 1995, 16(2-3), 157-182.

Zhang et al., "Intratumoral T Cells, Recurrence and Survival in Epithelial Ovarian Cancer", N. England J. Medicine, Jan. 16, 2003, 348(3), 203-213.

Wells, "Additivity of Mutational Effects in Proteins", Biochemistry, Sep. 18, 1990, 29, 8509-8517.

Ngo et al., "Computational complexity, protein structure prediction, and the Levinthal paradox", The Protein Folding Problems and Tertiary Structure Prediction, 1994, 492-495.

Skolnick et al., "From genes to protein structure and function: novel applications of computational approaches in the genomic era", Trends in Biotech, Jan. 2000, 18(1), 34-39.

Doerks et al., "Protein annotation: detective work for function prediction", Trends in Genetics, Jun. 1998, 14(6), 248-250.

* cited by examiner

SEQUENCE LISTING

```
<160> NUMBER OF SEQ ID NOS: 10

<210> SEQ ID NO 1
<211> LENGTH: 162
<212> TYPE: PRT
<213> ORGANISM: Homo sapiens

<400> SEQUENCE: 1

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 2
<211> LENGTH: 133
<212> TYPE: PRT
<213> ORGANISM: Homo sapiens

<400> SEQUENCE: 2

Gln Gly Gln Asp Arg His Met Ile Arg Met Arg Gln Leu Ile Asp Ile
1               5                   10                  15
```

```
Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                   40                   45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
                115                 120                 125

Gly Ser Glu Asp Ser
         130
```

<210> SEQ ID NO 3
<211> LENGTH: 129
<212> TYPE: PRT
<213> ORGANISM: Artificial
<220> FEATURE:
<223> OTHER INFORMATION: IL-21 variant

<400> SEQUENCE: 3

```
Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                   40                   45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Gln Lys His Arg Leu Thr Cys Pro Ser Cys Asp Ser Tyr Glu
                 85                  90                  95

Lys Lys Pro Pro Lys Glu Phe Leu Glu Arg Phe Lys Ser Leu Leu Gln
                100                 105                 110

Lys Met Ile His Gln His Leu Ser Ser Arg Thr His Gly Ser Glu Asp
                115                 120                 125

Ser
```

<210> SEQ ID NO 4
<211> LENGTH: 127
<212> TYPE: PRT
<213> ORGANISM: Artificial
<220> FEATURE:
<223> OTHER INFORMATION: IL-21 variant

<400> SEQUENCE: 4

```
Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                   40                   45
```

```
Cys Phe Gln Lys Ala Gln Leu Lys Ser Ala Asn Thr Gly Asn Asn Glu
     50                  55                  60

Arg Ile Ile Asn Val Ser Ile Lys Lys Leu Lys Arg Lys Pro Pro Ser
 65                  70                  75                  80

Thr Asn His Arg Leu Thr Cys Pro Ser Cys Asp Ser Tyr Glu Lys Lys
                 85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
            115                 120                 125

<210> SEQ ID NO 5
<211> LENGTH: 125
<212> TYPE: PRT
<213> ORGANISM: Artificial
<220> FEATURE:
<223> OTHER INFORMATION: Il-21 variant

<400> SEQUENCE: 5

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Leu Thr Cys Pro Ser Cys Asp Ser Tyr Glu Lys Lys Pro Pro
                85                  90                  95

Lys Glu Phe Leu Glu Arg Phe Lys Ser Leu Leu Gln Lys Met Ile His
            100                 105                 110

Gln His Leu Ser Ser Arg Thr His Gly Ser Glu Asp Ser
            115                 120                 125

<210> SEQ ID NO 6
<211> LENGTH: 126
<212> TYPE: PRT
<213> ORGANISM: Artificial
<220> FEATURE:
<223> OTHER INFORMATION: IL-21 variant

<400> SEQUENCE: 6

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr His Arg Leu Thr Cys Pro Ser Cys Asp Ser Tyr Glu Lys Lys Pro
                85                  90                  95

Pro Lys Glu Phe Leu Glu Arg Phe Lys Ser Leu Leu Gln Lys Met Ile
            100                 105                 110
```

-continued

```
His Gln His Leu Ser Ser Arg Thr His Gly Ser Glu Asp Ser
        115                 120                 125

<210> SEQ ID NO 7
<211> LENGTH: 127
<212> TYPE: PRT
<213> ORGANISM: Artificial
<220> FEATURE:
<223> OTHER INFORMATION: IL-21 variant

<400> SEQUENCE: 7

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Asn Leu Trp Gly
65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
        115                 120                 125

<210> SEQ ID NO 8
<211> LENGTH: 127
<212> TYPE: PRT
<213> ORGANISM: Artificial
<220> FEATURE:
<223> OTHER INFORMATION: IL-21 variant

<400> SEQUENCE: 8

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Leu Lys Arg Leu Asp Arg Asn Leu Trp Gly
65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
        115                 120                 125

<210> SEQ ID NO 9
<211> LENGTH: 127
<212> TYPE: PRT
<213> ORGANISM: Artificial
<220> FEATURE:
<223> OTHER INFORMATION: IL-21 variant

<400> SEQUENCE: 9
```

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
        50                  55                  60

Arg Ile Ile Asn Val Ser Leu Lys Arg Leu Asp Arg Asn Leu Trp Gly
65                  70                  75                  80

Leu Ala Gly Leu Asn Ser Cys Pro Ser Cys Asp Ser Tyr Glu Lys Lys
                85                  90                  95

Pro Pro Lys Glu Phe Leu Glu Arg Phe Lys Ser Leu Leu Gln Lys Met
            100                 105                 110

Ile His Gln His Leu Ser Ser Arg Thr His Gly Ser Glu Asp Ser
            115                 120                 125

<210> SEQ ID NO 10
<211> LENGTH: 126
<212> TYPE: PRT
<213> ORGANISM: Artificial
<220> FEATURE:
<223> OTHER INFORMATION: IL-21 variant

<400> SEQUENCE: 10

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Asn Leu Trp Gly
65                  70                  75                  80

Leu Ala Gly Leu Asn Ser Cys Pro Val Asp Ser Tyr Glu Lys Lys Pro
                85                  90                  95

Pro Lys Glu Phe Leu Glu Arg Phe Lys Ser Leu Leu Gln Lys Met Ile
            100                 105                 110

His Gln His Leu Ser Ser Arg Thr His Gly Ser Glu Asp Ser
            115                 120                 125
```

IL-21 VARIANTS

CROSS REFERENCE TO RELATED APPLICATIONS

This application is a national stage entry of PCT/EP2007/061543, filed on Oct. 26, 2007, which claims priority to European patent application No. 06123040.5, filed on Oct. 26, 2006, the contents of which are incorporated herein by reference in its entirety.

FIELD OF THE INVENTION

The present invention is concerned with new variants of IL-21, said variants having an improved binding to the IL-21 receptor.

BACKGROUND OF THE INVENTION

IL-21 peptides were first disclosed in WO 2000/53761, the polypeptide as encoded by the human IL-21 gene was shown in that application as SEQ ID No. 2. This pro-peptide is a 161 amino acid residue peptide. For convenience, the sequence is repeated in the present application as SEQ ID No. 1. It was initially believed that the mature peptide was the peptide consisting of amino acids residues 33 to 162 of SEQ ID No. 1; however more recently (WO 2004/112703) it has been suggested that the mature peptide is, in fact, amino acids residues 30 to 162 as shown in SEQ ID No. 2. IL-21 has been described as useful for the treatment of cancer, such as for instance malign melanoma. See for instance WO 2005/53761 and WO 2003/103589.

In spite of the efficacy shown by IL-21 in the treatment of various diseases, there remains a need for variants of IL-21 with improved or alternative properties, such as activity, selectivity, stability, and circulation time or biological half-life, to fulfil medical needs. Antagonism of the IL-21 receptor has also been described as having therapeutic use.

International Application WO2004/112703 describes a number of IL-21 variants.

International Application WO2006/111524 describes some IL-21 peptides which has improved binding to the IL-21 receptor.

SUMMARY OF THE INVENTION

It has now been found that the activity of IL-21 is largely maintained or even improved when the length of the region corresponding to amino acid residues 66 to 98 in SEQ ID No. 2 is reduced.

Correspondingly, the present invention relates to an IL-21 peptide, wherein the length of the region corresponding to amino acid residues 66 to 98 in SEQ ID No. 2 is reduced. In one embodiment, the invention relates to an IL-21 peptide, wherein the length of the region corresponding to amino acid residues 77 to 92 in SEQ ID No. 2 is reduced. In one embodiment, the invention relates to an IL-21 peptide, wherein the length of the region corresponding to amino acid residues 82 to 88 in SEQ ID No. 2 is reduced. In one embodiment, the invention relates to an IL-21 peptide, wherein the length of the region corresponding to amino acid residues 71 to 92 in SEQ ID No. 2 is reduced. In one embodiment, the invention relates to an IL-21 peptide, wherein the length of the region corresponding to amino acid residues 65 to 92 in SEQ ID No. 2 is reduced. In one embodiment, the invention relates to an IL-21 peptide, wherein the length of the region corresponding to amino acid residues 77 to 96 in SEQ ID No. 2 is reduced. In one embodiment, the invention relates to an IL-21 peptide, wherein the length of the region corresponding to amino acid residues 83 to 86 in SEQ ID No. 2 is reduced. In one embodiment, the invention relates to an IL-21 peptide, wherein the length of the region corresponding to amino acid residues 83 to 86 in SEQ ID No. 2 is reduced.

The present invention also relates to an IL-21 peptide, wherein the region corresponding to amino acid residues 66 to 98 in SEQ ID No. 2 has been replaced by a stretch of amino acid residues, or wherein the region corresponding to amino acid residues 77 to 92 in SEQ ID No. 2 has been replaced by a stretch of amino acid residues, wherein said stretch of amino acid residues is shorter than the region it is replacing.

In one embodiment, the invention provides the use of a peptide of the present invention in therapy.

In one embodiment, the invention relates to a pharmaceutical composition comprising a peptide of the present invention.

In one embodiment, the invention provides a therapeutic method, the method comprising the administration of a therapeutically effective amount of a peptide of the present invention to a patient in need thereof.

In one embodiment, the invention relates to the use of peptide of the present invention in the manufacture of a medicament.

In one embodiment, the invention relates to nucleic acid construct encoding a peptide of the present invention; to vectors comprising said constructs; and to host cells comprising said vectors.

In one embodiment, the invention relates to specific antibodies against a peptide of the present invention.

FIGURES

FIG. 1: Dose-response curves for huIL-21-WT and deletion variant [83-86]. Supernatants from HEK293 FS cells transfected with hIL-21 cDNA constructs were analyzed in a reporter assay using the Baf3/hIL-21Ra cells. The curves represent a single, yet representative experiment performed in triplicate. hIL-21NN is IL-21 WT.

Figure 2:
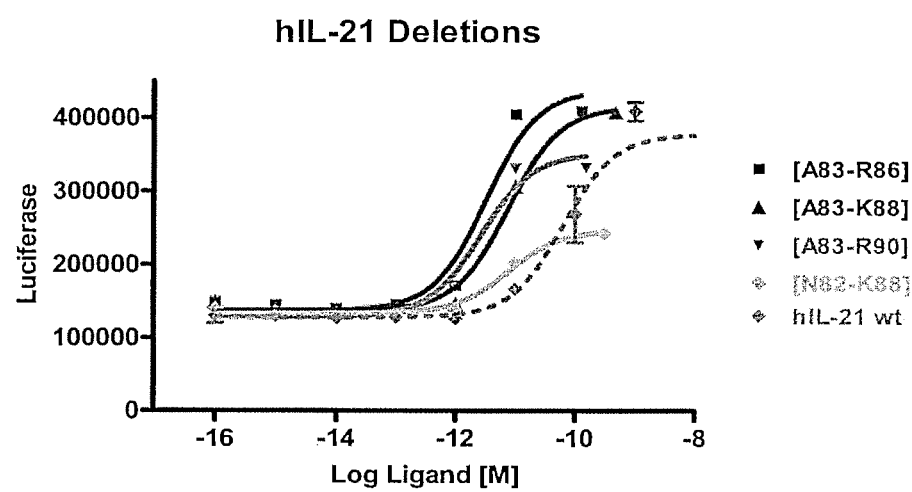

FIG. 2: Dose-response curves for huIL-21-WT and deletion variants as described on figure. Supernatants from HEK293 FS cells transfected with hIL-21 cDNA constructs were analyzed in a reporter assay using the Baf3/hIL-21Ra cells. The curves represent a single, yet representative experiment performed in triplicate. hIL-21NN is an IL-21 WT control.

Figure 3:
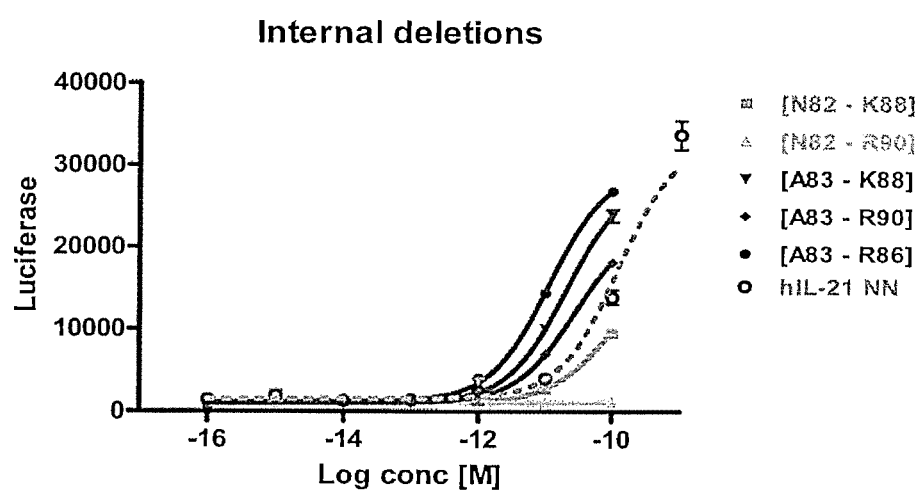

FIG. 3: Dose-response curves for huIL-21-WT and deletion variants as described on figure. Supernatants from HEK293 FS cells transfected with hIL-21 cDNA constructs were analyzed in a reporter assay using the Baf3/hIL-21Ra cells. The curves represent a single, yet representative experiment performed in triplicate.

DESCRIPTION OF THE INVENTION

It has now been found that the activity of IL-21 is largely maintained or even improved when the length of the region corresponding to amino acid residues 66 to 98 in SEQ ID No. 2 is reduced.

Correspondingly, the present invention relates to an IL-21 peptide, wherein the length of the region corresponding to amino acid residues 66 to 98 in SEQ ID No. 2 is reduced.

The term peptide includes any suitable peptide and may be used synonymously with the terms polypeptide and protein, unless otherwise stated or contradicted by context; provided that the reader recognize that each type of respective amino acid polymer-containing molecule may be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides in the context of the inventive methods and compositions described herein may comprise non-naturally occurring and/or non-L amino acid residues, unless otherwise stated or contradicted by context.

The term peptide, unless otherwise stated or contradicted by context, (and if discussed as individual embodiments of the term(s) polypeptide and/or protein) also encompasses derivatized peptide molecules. Briefly, in the context of the present invention, a derivative is a peptide in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives). Non-limiting examples of such amino acid residues include for instance 2-aminoadipic acid, 3-amino-adipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-di-aminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methyl-isoleucine, 6-N-methyllysine, N-methylvaline, norvaline, norleucine, ornithine, and statine halogenated amino acids.

IL-21 peptides refers to any peptide that specifically binds to the IL21 receptor under cellular and/or physiological conditions for an amount of time sufficient to induce, promote, enhance, and/or otherwise modulate a physiological effect associated with the antigen; to allow detection by ELISA, Western blot, or other similarly suitable protein binding technique described herein and/or known in the art and/or to otherwise be detectably bound thereto after a relevant period of time (for instance at least about 15 minutes, at least about 30 minutes, at least about 45 minutes, at least about 1 hour, at least about 2 hours, at least about 4 hours, at least about 6 hours, at least about 12 hours, about 1-24 hours, about 1-36 hours, about 1-48 hours, about 1-72 hours, about one week, or longer). The binding of the IL-21 peptide may for instance be determined as described in the examples.

In one embodiment, an IL-21 peptide of the invention has an amino acid sequence having at least 80% identity to SEQ ID No. 1 or SEQ ID No. 2. In one embodiment, an IL-21 peptide of the invention has an amino acid sequence having at least 85%, such as at least 90%, for instance at least 95%, such as for instance at least 99% identity to SEQ ID No. 1 or SEQ ID No. 2.

The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two peptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci. USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

In one embodiment, an IL-21 peptide of the invention has an amino acid sequence, which sequence is at least 80% similar to SEQ ID No. 1 or SEQ ID No. 2. In one embodiment, an IL-21 peptide of the invention has an amino acid sequence, which sequence is at least 85%, such as at least 90%, for instance at least 95%, such as for instance at least 99% identity to SEQ ID No. 1 or SEQ ID No. 2.

The term "similarity" is a concept related to identity, but in contrast to "identity", refers to a sequence relationship that includes both identical matches and conservative substitution matches. If two polypeptide sequences have, for example, (fraction (10/20)) identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ((fraction (15/20))). Therefore, in cases where there are conservative substitutions, the degree of similarity between two polypeptides will be higher than the percent identity between those two polypeptides.

Conservative modifications of a peptide comprising an amino acid sequence of SEQ ID No. 1 or SEQ ID No. 2 (and the corresponding modifications to the encoding nucleic acids) will produce peptides having functional and chemical characteristics similar to those of a peptide comprising an amino acid sequence of SEQ ID No. 1 or SEQ ID No. 2. In contrast, substantial modifications in the functional and/or chemical characteristics of peptides according to the invention as compared to a peptide comprising an amino acid sequence of SEQ ID No. 1 or SEQ ID No. 2 may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., Acta Physiol. Scand. Suppl. 643, 55-67 (1998); Sasaki et al., Adv. Biophys. 35, 1-24 (1998), which discuss alanine scanning mutagenesis).

Desired amino acid substitutions (whether conservative or non-conservative) may be determined by those skilled in the art at the time such substitutions are desired. For example, amino acid substitutions can be used to identify important residues of the peptides according to the invention, or to increase or decrease the affinity of the peptides described herein for the receptor in addition to the already described mutations.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157, 105-131 (1982). It is known that certain amino acids may be substituted for other amino acids having a similar hydropathic index or score and still retain a similar biological activity. In making changes based upon the hydropathic index, the substitution of amino acids whose hydropathic indices are within .±2 is preferred, those that are within ±1 are particularly preferred, and those within ±0.5 are even more particularly preferred.

It is also understood in the art that the substitution of like amino acids may be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine ('3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions.".

Peptides of the present invention may also comprise non-naturally occurring amino acids.

In one embodiment of the invention, the length of the region corresponding to amino acid residues 66 to 98 in SEQ ID No. 2 is reduced by at least 1, such as at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as at least 19, such as at least 20, such as at least 21, such as at least 22, such as at least 23, such as at least 24, such as at least 25, such as at least 26, such as at least 27, such as at least 28, such as at least 29, such as at least 30, such as at least 31, such as at least 32 amino acid residues.

In one embodiment, the invention relates to an IL-21 peptide, wherein the length of the region corresponding to amino acid residues 77 to 92 in SEQ ID No. 2 is reduced.

In one embodiment, the length of the region corresponding to amino acid residues 77 to 92 in SEQ ID No. 2 is reduced by at least 1, such as at least 2, such as at least 3, such as at least 4, such as at least 5, such as at least 6, such as at least 7, such as at least 8, such as at least 9, such as at least 10, such as at least 11, such as at least 12, such as at least 13, such as at least 14 amino acid residues.

In one embodiment, the invention relates to an IL-21 peptide, wherein the length of the region corresponding to amino acid residues 83 to 90 in SEQ ID No. 2 is reduced.

In one embodiment, the length of the region corresponding to amino acid residues 83 to 90 in SEQ ID No. 2 is reduced by at least 1, such as at least 2, such as at least 3, such as at least 4, such as at least 5, such as at least 6, such as at least 7 amino acid residues.

In one embodiment, the invention relates to an IL-21 peptide, wherein the length of the region corresponding to amino acid residues 82 to 88 in SEQ ID No. 2 is reduced.

In one embodiment, the length of the region corresponding to amino acid residues 82 to 88 in SEQ ID No. 2 is reduced by at least 1, such as at least 2, such as at least 3, such as at least 4, such as at least 5 amino acid residues.

In one embodiment, the invention relates to an IL-21 peptide, wherein the length of the region corresponding to amino acid residues 71 to 92 in SEQ ID No. 2 is reduced.

In one embodiment, the length of the region corresponding to amino acid residues 71 to 92 in SEQ ID No. 2 is reduced by at least 1, such as at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as at least 19, such as at least 20 amino acid residues.

In one embodiment, the invention relates to an IL-21 peptide, wherein the length of the region corresponding to amino acid residues 65 to 92 in SEQ ID No. 2 is reduced.

In one embodiment, the length of the region corresponding to amino acid residues 65 to 92 in SEQ ID No. 2 is reduced by at least 1, such as at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as at least 19, such as at least 20, such as at least 21, such as at least 22, such as at least 23, such as at least 24, such as at least 25, such as at least 26, such as at least 27 amino acid residues.

In one embodiment, the invention relates to an IL-21 peptide, wherein the length of the region corresponding to amino acid residues 77 to 96 in SEQ ID No. 2 is reduced.

In one embodiment, the length of the region corresponding to amino acid residues 77 to 96 in SEQ ID No. 2 is reduced by at least 1, such as at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as at least 19 amino acid residues.

In one embodiment, the invention relates to an IL-21 peptide, wherein the length of the region corresponding to amino acid residues 83 to 86 in SEQ ID No. 2 is reduced.

In one embodiment, the length of the region corresponding to amino acid residues 83 to 86 in SEQ ID No. 2 is reduced by at least 1, such as at least 2, such as at least 3 amino acid residues.

In one embodiment, the invention relates to an IL-21 peptide, wherein the length of the region corresponding to amino acid residues 83 to 86 in SEQ ID No. 2 is reduced.

In one embodiment, the length of the region corresponding to amino acid residues 83 to 86 in SEQ ID No. 2 is reduced by at least 1, such as at least 2, such as at least 3, such as at least 4, such as at least 5 amino acid residues.

In one embodiment, the length is reduced by the deletion of the necessary amount of amino acid residues in the mentioned region. In one embodiment, said deleted amino acid residues were not all adjacent to each other in the amino acid sequence of said region.

The present invention also relates to an IL-21 peptide, wherein the region corresponding to amino acid residues 66 to 98 in SEQ ID No. 2 has been replaced by a stretch of amino acid residues, or wherein the region corresponding to amino acid residues 77 to 92 in SEQ ID No. 2 has been replaced by a stretch of amino acid residues, wherein said stretch of amino acid residues is at least 1, such as at least 2, for instance at least 3, such as at least 4, for instance at least 5, such as at least 6, for instance at least 7, such as at least 8, for instance at least 9, such as at least 10, for instance at least 11, such as at least 12, for instance at least 13, such as at least 14, for instance at least 15 amino acid residue shorter than the region it is replacing. Said stretch of amino acid residues may be of IL-21 origin or of non-IL-21 origin. The essential feature of said stretch is that it is at least 1 amino acid residue shorter than the stretch it is replacing. The exact sequence of said stretch of amino acid residues is not important, the essential part is that it is shorter than the region it is replacing. The sequence of said stretch of amino acid residues may for instance be of IL-21 origin or of non-IL-21-origin.

In one embodiment, said stretch of amino acid residues is of IL-21 origin. In one embodiment, said stretch of amino acid residues has a sequence, which originates from within the region corresponding to amino acid residues 66 to 98 in SEQ ID No. 2. Sequences originating from this region of IL-21 may for instance be obtained by substitution of one or more amino acid residues within this region with other amino acid residues. The nature of the substitution is not of importance, since it is the length of the stretch of amino acid residues (shorter than the region which it is replacing), that is of importance. Said stretch of amino acid residues of IL-21 origin will also comprise deletions as compared to the region corresponding to amino acid residues 66 to 98 in SEQ ID No. 2 in order to achieve the shorter length and such deletions may be spread out throughout the region or may be of amino acid residues adjacent to each other.

In one embodiment, the stretch of amino acid residues of IL-21 origin is a stretch of amino acid residues having a sequence which is at least 50%, for instance at least 60%, such as at least 70%, for instance at least 80%, such as at least 85%, for instance at least 90%, such as at least 95% identical or similar to a sequence of amino acid residues within the region of amino acid residues 66 to 98 in SEQ ID No. 2.

In one embodiment, said stretch of amino acid residues comprises at least one non-conservative substitution of an amino acid residue present in the region corresponding to amino acid residues 66 to 98 in SEQ ID No. 2. In one embodiment, said stretch of amino acid residues comprises a deletion of amino acids 77 to 92 of SEQ ID No. 2. In one embodiment, said stretch of amino acid residues comprises a deletion of amino acids 83 to 90 of SEQ ID No. 2. In one embodiment, said stretch of amino acid residues comprises a deletion of amino acids 82 to 88 of SEQ ID No. 2. In one embodiment, said stretch of amino acid residues comprises a deletion of amino acids 71 to 92 of SEQ ID No. 2. In one embodiment, said stretch of amino acid residues comprises a deletion of amino acids 65 to 92 of SEQ ID No. 2. In one embodiment, said stretch of amino acid residues comprises a deletion of amino acids 77 to 96 of SEQ ID No. 2. In one embodiment, said stretch of amino acid residues comprises a deletion of amino acids 83 to 86 of SEQ ID No. 2. In one embodiment, said stretch of amino acid residues comprises a deletion of amino acids 83 to 88 of SEQ ID No. 2. In one embodiment, said stretch of amino acid residues comprises one or more non-adjacent deletions in the region corresponding to amino acid residues 66 to 98 in SEQ ID No. 2.

In one embodiment, the stretch of amino acid residues of IL-21 origin is a stretch of amino acid residues having a sequence which is at least 50%, for instance at least 60%, such as at least 70%, for instance at least 80%, such as at least 85%, for instance at least 90%, such as at least 95% identical or similar to a sequence of amino acid residues within the region of amino acid residues 77 to 92 in SEQ ID No. 2. In one embodiment, said stretch of amino acid residues comprises at least one non-conservative substitution of an amino acid residue present in the region corresponding to amino acid residues 77 to 92 in SEQ ID No. 2. In one embodiment, said stretch of amino acid residues comprises at least one non-conservative substitution of an amino acid residue present in the region corresponding to amino acid residues 77 to 92 in SEQ ID No. 2. In one embodiment, said stretch of amino acid residues comprises a deletion of amino acids 83 to 90 of SEQ ID No. 2. In one embodiment, said stretch of amino acid residues comprises a deletion of amino acids 82 to 88 of SEQ ID No. 2. In one embodiment, said stretch of amino acid residues comprises a deletion of amino acids 83 to 86 of SEQ ID No. 2. In one embodiment, said stretch of amino acid residues comprises a deletion of amino acids 83 to 88 of SEQ ID No. 2. In one embodiment, said stretch of amino acid residues comprises one or more non-adjacent deletions in the region corresponding to amino acid residues 77 to 92 in SEQ ID No. 2.

In one embodiment, said stretch of amino acid residues is of non-IL-21 origin. Such a stretch of amino acid residues may for instance have a sequence which is less than 50% identical to any sequence of similar length in SEQ ID No. 2. For the purpose of the present invention, said stretch of amino acid residues may also have a sequence, which is less than 50% identical to the sequence of amino acid residues 65 to 96 of SEQ ID No. 2 and/or a sequence which is less than 50% identical to the sequence of amino acid residues 77 to 92 of SEQ ID No. 2. Again, the exact sequence of said stretch of amino acid residues is not important, the essential part is that it is shorter than the region it is replacing.

In one embodiment, the invention relates to any of the IL-21 peptides described above, with the provisio that the IL-21 peptide does not have the sequence of SEQ ID No. 3, 4, 5 or 6 or the sequence of a peptide having the sequence of SEQ ID No. 3, 4, 5 or 6 with an additional N-terminal methionine. In one embodiment, the invention relates to any of the IL-21 peptides described above, with the provisio that the IL-21 peptide does not have the sequence of SEQ ID No. 7, 8, 9 or 10 or the sequence of a peptide having the sequence of SEQ ID No. 7, 8, 9 or 10 with an additional N-terminal methionine. Peptides having the sequence of SEQ ID No. 3, 4, 5, 6, 7, 8, 9, and 10 are described in International Application WO2004/112703.

In one embodiment, the invention relates to any of the IL-21 peptides described above, with the provisio that the IL-21 peptide does not have a substitution mutation in the position corresponding to Asn-68 in SEQ ID No. 2.

In one embodiment, the invention relates to any of the IL-21 peptides described above, with the provisio that the amino acid residue in the position corresponding to Asn-68 in SEQ ID No. 2 is not a Gln.

In one embodiment, the invention relates to any of the IL-21 peptides described above, with the provisio that the IL-21 peptide does not have a substitution mutation in the position corresponding to Ser-80 in SEQ ID No. 2.

In one embodiment, the invention relates to any of the IL-21 peptides described above, with the provisio that the amino acid residue in the position corresponding to Ser-80 in SEQ ID No. 2 is not a Thr.

In one embodiment, the invention relates to any of the IL-21 peptides described above, with the provisio that the IL-21 peptide does not have a substitution mutation in the position corresponding to Gln-87 in SEQ ID No. 2.

In one embodiment, the invention relates to any of the IL-21 peptides described above, with the provisio that the amino acid residue in the position corresponding to Gln-87 in SEQ ID No. 2 is not a Asn.

In one embodiment, the invention relates to any of the IL-21 peptides described above, with the provisio that the IL-21 peptide does not have substitution mutation in the position corresponding to Asn-68, in the position corresponding to Ser-80 in SEQ ID No. 2 and in the position corresponding to Gln-87 in SEQ ID No. 2.

In one embodiment, the invention relates to any of the IL-21 peptides described above, with the provisio that the amino acid residue in the position corresponding to Asn-68 in SEQ ID No. 2 is not a Gln, the amino acid residue in the position corresponding to Ser-80 in SEQ ID No. 2 is not a Thr and the amino acid residue in the position corresponding to Gln-87 in SEQ ID No. 2 is not a Asn.

In one embodiment, the invention relates to nucleic acid construct encoding a peptide of the present invention; to vectors comprising said constructs; and to host cells comprising said vectors.

In one embodiment, the invention relates to a specific antibody against a peptide of the present invention. In one embodiment, said antibody does not bind to a polypeptide having the amino acid sequence of SEQ ID No. 1, 2, 3, 4, 5, 6, 7, 8, 9, or 10 or to any of the polypeptides described in International Application WO2004/112703.

When peptides are expressed in mammalian cells, such as CHO cells, an N-terminal signal peptide is often removed by a so-called signal peptidase leading to the mature peptide. It is well-known in the art that to express the same heterologous peptides in prokaryotic cells, such as e.g. *E. coli*, it is often necessary—via recombinant technology well-known to those skilled in the art—to introduce an additional N-terminal methionine to the sequence of the mature peptide. The present invention is thus intended to include the above mentioned peptides with or without an N-terminal methionine.

In one embodiment, the invention is related to pharmaceutically acceptable salts of the above peptides.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The peptides of the present invention may be further derivatized by the attachment of groups which will effect an extension of the circulation time in plasma and/or biological half-life, or which will reduce any immunogenicity. It is well-known in the art that such effects may be obtained by the attachment of certain groups, such as polyethylene glycol (PEG); lipophilic groups, such as fatty acids; plasma proteins, such as albumin; or albumin binding moieties. For examples from the art, see e.g. WO 01/79271, U.S. Pat. No. 5,739,208, and WO 03/44056.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a protein of interest. The construct may optionally contain other nucleic acid segments.

The nucleic acid construct of the invention encoding the protein of the invention may suitably be of genomic or cDNA origin, for instance obtained by preparing a genomic or cDNA library and screening for DNA sequences coding for all or part of the protein by hybridization using synthetic oligonucleotide probes in accordance with standard techniques (cf. Sambrook et al., Molecular Cloning: A Laboratory Manual, Cold Spring Harbor, N.Y.). For the present purpose, the DNA sequence encoding the protein may be of human origin, i.e. derived from a human genomic DNA or cDNA library. In particular, the DNA sequence may be of human origin, e.g. cDNA from a particular human organ or cell type or a gene derived from human genomic DNA. The nucleic acid construct of the invention encoding the peptide may also be prepared synthetically by established standard methods, e.g. the phosphoamidite method or by polymerase chain reaction using specific primers. Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

In one embodiment, the nucleic acid construct is a DNA construct which term will be used in the following.

In one embodiment, the present invention relates to a recombinant vector comprising a DNA construct of the invention. The recombinant vector into which the DNA construct of the invention is inserted may be any vector, for instance an expression vector, which may conveniently be subjected to recombinant DNA procedures as it is known in the art. The procedures used to ligate the DNA sequences coding for the present protein and the vector sequences, including for instance promoter and optionally the terminator and/or secretory signal sequences are well known to persons skilled in the art (cf., for instance, Sambrook et al., op.cit.).

The host cell into which the DNA construct or the recombinant vector of the invention is introduced may be any cell which is capable of producing the present protein and includes bacteria, yeast, fungi and higher eukaryotic cells as it is known in the art. The transformed or transfected host cell is then cultured in a suitable nutrient medium under conditions permitting the expression of the present protein, after which the resulting protein is recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The protein produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of protein in question.

Peptides of the present invention may be used to raise antibodies that specifically bind to the peptides of the present invention. In the present context, "antibodies" include monoclonal and polyclonal antibodies, and antigen-binding fragments thereof, such as F(ab')$_2$ and Fab fragments, including genetically engineered antibodies and humanized antibodies. Antibodies are said to be specific if they bind to a peptide of the present invention with a $K_a$ greater than or equal to $10^7$ $M^{-1}$. Methods for preparing antibodies are disclosed in e.g. Hurrell J. G. R. (Ed.) Monoclonal Hybridoma Antibodies: Techniques and Applications, CRC Press, Boca Raton, Fla., 1982 and Sambrok, Molecular Cloning: A Laboratory Manual, Cold Spring Harbour, New York, 1989.

IL-21 has been implicated in the treatment of viral diseases, such as hepatitis B Virus, Hepatitis C virus, Human Immunodeficiency Virus, Respiratory Syncytial Virus, Epp-stein-Barr Virus, Influenza Virus, Cytomegalovirus, HerpesVirus and Severe Acute Respiratory Syndrome; allergic diseases, such as asthma, allergic rhinitis or allergic diseases in the skin; parasitic diseases, such as helminthic infection, autoimmune diseases, such as allograft rejection and diabetes; and cancer, such as colorectal cancer, renal cell carcinoma, Non-Hodgkin's lymphoma, epithelial cancer, breast cancer, prostate cancer, ovarian cancer, colon cancer and melanoma (WO 2003/103589). Antagonism of the IL-21 receptor has also been implicated in the treatment of inflammatory diseases, such as for instance autoimmune diseases, for instance systemic lupus erythematosus (SLE), rheumatoid arthritis (RA) and inflammatory bowel disease (IBD). In one embodiment, an IL-21 peptide of the present invention is an agonist of the IL-21 and is useful for treating diseases, where agonism of the IL-21 receptor is considered beneficial. In one embodiment, an IL-21 peptide of the present invention is an antagonist of the IL-21 receptor and is useful for treating diseases, where antagonism of the IL-21 receptor is considered beneficial.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active peptides to prevent the onset of the symptoms or complications. The patient to be treated may be a mammal, in particular a human being, but it may also include animals, such as dogs, cats, cows, sheep and pigs. It is to be understood, that therapeutic and prophylactic (preventive) regimes represent separate aspects of the present invention.

Consequently, in one embodiment, the invention provides the use of a peptide of the present invention in therapy.

In one embodiment, the invention provides the use of a peptide of the present invention, which peptide is an agonist of IL-21, in the treatment of cancer.

In the present context, "cancer" refers to any neoplastic disorder, including such cellular disorders such as sarcoma, carcinoma, melanoma, leukemia, lymphoma, cancers in the breast, head and neck, ovaries, bladder, lung, pharynx, larynx, oesophagus, stomach, small intestines, liver, pancreas, colon, female reproductive tract, male reproductive tract, prostate, kidneys and central nervous system. In particular, "cancer" is intended to indicate non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

In more specific embodiments of the invention the terms "neoplastic disorders", "cancer" or "tumor growth" are to be understood as referring to all forms of neoplastic cell growth, including both cystic and solid tumors, bone and soft tissue tumors, including both benign and malignant tumors, including tumors in anal tissue, bile duct, bladder, blood cells, bone, bone (secondary), bowel (colon & rectum), brain, brain (secondary), breast, breast (secondary), carcinoid, cervix, children's cancers, eye, gullet (oesophagus), head & neck, kaposi's sarcoma, kidney, larynx, leukaemia (acute lymphoblastic), leukaemia (acute myeloid), leukaemia (chronic lymphocytic), leukaemia (chronic myeloid), leukaemia (other), liver, liver (secondary), lung, lung (secondary), lymph nodes (secondary), lymphoma (hodgkin's), lymphoma (non-hodgkin's), melanoma, mesothelioma, myeloma, ovary, pancreas, penis, prostate, skin, soft tissue sarcomas, stomach, testes, thyroid, unknown primary tumour, vagina, vulva, womb (uterus).

Soft tissue tumors include Benign schwannoma Monosomy, Desmoid tumor, Lipoblastoma, Lipoma, Uterine leiomyoma, Clear cell sarcoma, Dermatofibrosarcoma, Ewing sarcoma, Extraskeletal myxoid chondrosarcoma, Liposarcoma myxoid, Liposarcoma, well differentiated, Alveolar rhabdomyosarcoma, and Synovial sarcoma.

Specific bone tumor include Nonossifying Fibroma, Unicameral bone cyst, Enchondroma, Aneurysmal bone cyst, Osteoblastoma, Chondroblastoma, Chondromyxofibroma, Ossifying fibroma and Adamantinoma, Giant cell tumor, Fibrous dysplasia, Ewing's Sarcoma, Eosinophilic Granuloma, Osteosarcoma, Chondroma, Chondrosarcoma, Malignant Fibrous Histiocytoma, and Metastatic Carcinoma.

Leukaemias refers to cancers of the white blood cells which are produced by the bone marrow. This includes but are not limited to the four main types of leukaemia; acute lymphoblastic (ALL), acute myeloblastic (AML), chronic lymphocytic (CLL) and chronic myeloid (CML).

In one embodiment, the cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin. In a more specific embodiment, the cancer is malignant melanoma.

In one embodiment, the invention provides the use of a peptide of the present invention, which is an antagonist of IL-21 in the treatment of an autoimmune disease, such as for instance systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as PV (pemphigus vulgaris), psoriasis, atopic dermatitis, celiac disease, hashimoto's thyroiditis, graves' disease (thyroid), sjogren's syndrome, guillain-barre syndrome, goodpasture's syndrome, additon's disease, wegener's granulomatosis, primary biliary sclerosis, sclerosing cholangitis, autoimmune hepatitis, polymyalgia rheumatica, paynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia greata, and vitilgo. Other examples can be found in PCT application WO01/46420, which is directed at the use of IL-17 for treatment of autoimmune and/or inflammatory diseases and wherein several examples of such diseases are given.

In one embodiment, the invention relates to a pharmaceutical composition comprising a peptide of the present invention.

In one embodiment, the invention provides a therapeutic method, the method comprising the administration of a therapeutically effective amount of a peptide of the present invention to a patient in need thereof.

A "therapeutically effective amount" of a peptide as used herein means an amount sufficient to cure, alleviate or partially arrest the clinical manifestations of a given disease and its complications. An amount adequate to accomplish this is defined as "therapeutically effective amount". Effective amounts for each purpose will depend on the type and severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In one embodiment, the invention relates to the use of peptide of the present invention in the manufacture of a medicament.

In one embodiment, the invention relates to methods of treating viral infections, allergic diseases, autoimmune diseases and cancer as listed above, the method comprising the administration of an effective amount of a peptide of the present invention to a patient in need thereof.

In one embodiment, the present invention relates to the use of a peptide of the present invention for the manufacture of a medicament for the treatment of viral infections, allergic diseases, autoimmune diseases or cancer as described above.

It is well-known in the art that for instance cancer treatment regimes often include more than one medicament or treatment modality. In one embodiment, the present invention therefore provides a method for the treatment of cancer, the method comprising the administration of an effective amount of a peptide of the present invention in combination with an effective amounts of another medicament useful for the treatment of cancer. In the present invention, 'in combination with' means that a peptide of the invention is administered (i) before, (ii) at the same time and/or (iii) after treatment with one or more of the following. Examples of medicaments and treatments which may be combined with the use of an effective amount of a peptide according to the invention can be found in for instance WO 2005/037306, WO 2003103589, WO 2005113001 and PCT/US2007/73506.

Pharmaceutical Compositions

The present invention also provides a pharmaceutical composition comprising a peptide of the present invention which is present in a concentration from $10^{-15}$ mg/ml to 200 mg/ml, such as $10^{-10}$ mg/ml-5 mg/ml, and wherein said formulation has a pH from 2.0 to 10.0. Optionally, said formulation may comprise one or more further cancer agents as described above. The formulation may further comprise a buffer system, preservative(s), tonicity agent(s), chelating agent(s), stabilizers and surfactants. In one embodiment of the invention the pharmaceutical composition is an aqueous formulation, i.e. formulation comprising water. Such formulation is typically a solution or a suspension. In one embodiment of the invention the pharmaceutical composition is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water. In one embodiment the pharmaceutical composition is a freeze-dried formulation, whereto the physician or the patient adds solvents and/or diluents prior to use. In one embodiment the pharmaceutical composition is a dried formulation (e.g. freeze-dried or spray-dried) ready for use without any prior dissolution.

In one embodiment the invention relates to a pharmaceutical composition comprising an aqueous solution of a peptide of the present invention, and a buffer, wherein said IL-21 protein is present in a concentration from 0.1-100 mg/ml, and wherein said formulation has a pH from about 2.0 to about 10.0. Designing a pharmaceutical composition according to the present invention comprising an IL-21 variant peptide of the invention is within the knowledge of a person skilled in the art. The selection of pH, which buffer to use, whether to add preservatives, isotonic agents, chelating agents, stabilizers, surfactants, agents to prevent aggregate formation, inhibitors of oxidation of methionine residues to methionine sulfoxide, etc are thus within the knowledge of a person skilled in the art to determine. It is possible that other ingredients may be present in a pharmaceutical composition of the present invention. Such additional ingredients may include wetting agents, emulsifiers, antioxidants, bulking agents, tonicity modifiers, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical composition of the present invention and it is within the knowledge of a person skilled in the art to design an acceptable pharmaceutical composition with due considerations to the administration method and dosage forms and regimes.

Pharmaceutical compositions containing an IL-21 variant peptide of the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment. Pharmaceutical compositions of the present invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants. Pharmaceutical compositions of the invention may further be compounded in, or attached to, for example through covalent, hydrophobic and electrostatic interactions, a drug carrier, drug delivery system and advanced drug delivery system in order to further enhance stability of the peptide of the present invention, increase bioavailability, increase solubility, decrease adverse effects, achieve chronotherapy well known to those skilled in the art, and increase patient compliance or any combination thereof. Pharmaceutical compositions of the present invention are useful in the pharmaceutical composition of solids, semisolids, powder and solutions for pulmonary administration of a peptide of the present invention, using, for example a metered dose inhaler, dry powder inhaler and a nebulizer, all being devices well known to those skilled in the art. Pharmaceutical compositions of the present invention may also be useful in the formulation of controlled, sustained, protracting, retarded, and slow release drug delivery systems.

The following is a list of embodiments of the present invention.

Embodiment 1

An IL-21 peptide, wherein the length of the region corresponding to amino acid residues 66 to 98 in SEQ ID No. 2 is reduced.

Embodiment 2

A peptide according to embodiment 1, wherein the length of the region corresponding to amino acid residues 66 to 98 in SEQ ID No. 2 is reduced by at least 1 amino acid residue.

Embodiment 3

A peptide according to embodiment 2, wherein the length of the region corresponding to amino acid residues 66 to 98 in SEQ ID No. 2 is reduced by at least 2 amino acid residues.

Embodiment 4

A peptide according to embodiment 3, wherein the length of the region corresponding to amino acid residues 66 to 98 in SEQ ID No. 2 is reduced by at least 3 amino acid residues.

Embodiment 5

A peptide according to embodiment 4, wherein the length of the region corresponding to amino acid residues 66 to 98 in SEQ ID No. 2 is reduced by at least 4 amino acid residues.

Embodiment 6

An IL-21 peptide, wherein the length of the region corresponding to amino acid residues 77 to 92 in SEQ ID No. 2 is reduced.

Embodiment 7

A peptide according to embodiment 6, wherein the length of the region corresponding to amino acid residues 77 to 92 in SEQ ID No. 2 is reduced by at least 1 amino acid residue.

Embodiment 8

A peptide according to embodiment 7, wherein the length of the region corresponding to amino acid residues 77 to 92 in SEQ ID No. 2 is reduced by at least 2 amino acid residues.

Embodiment 9

A peptide according to embodiment 8, wherein the length of the region corresponding to amino acid residues 77 to 92 in SEQ ID No. 2 is reduced by at least 3 amino acid residues.

Embodiment 10

A peptide according to embodiment 9, wherein the length of the region corresponding to amino acid residues 77 to 92 in SEQ ID No. 2 is reduced by at least 4 amino acid residues.

Embodiment 11

An IL-21 peptide, wherein the length of the region corresponding to amino acid residues 83 to 90 in SEQ ID No. 2 is reduced.

Embodiment 12

A peptide according to embodiment 11, wherein the length of the region corresponding to amino acid residues 83 to 90 in SEQ ID No. 2 is reduced by at least 1 amino acid residue.

Embodiment 13

A peptide according to embodiment 12, wherein the length of the region corresponding to amino acid residues 83 to 90 in SEQ ID No. 2 is reduced by at least 2 amino acid residues.

Embodiment 14

A peptide according to embodiment 13, wherein the length of the region corresponding to amino acid residues 83 to 90 in SEQ ID No. 2 is reduced by at least 3 amino acid residues.

Embodiment 15

A peptide according to embodiment 14, wherein the length of the region corresponding to amino acid residues 83 to 90 in SEQ ID No. 2 is reduced by at least 4 amino acid residues.

Embodiment 16

An IL-21 peptide, wherein the length of the region corresponding to amino acid residues 82 to 88 in SEQ ID No. 2 is reduced.

Embodiment 17

A peptide according to embodiment 16, wherein the length of the region corresponding to amino acid residues 82 to 88 in SEQ ID No. 2 is reduced by at least 1 amino acid residue.

Embodiment 18

A peptide according to embodiment 17, wherein the length of the region corresponding to amino acid residues 82 to 88 in SEQ ID No. 2 is reduced by at least 2 amino acid residues.

Embodiment 19

A peptide according to embodiment 18, wherein the length of the region corresponding to amino acid residues 82 to 88 in SEQ ID No. 2 is reduced by at least 3 amino acid residues.

Embodiment 20

A peptide according to embodiment 19, wherein the length of the region corresponding to amino acid residues 82 to 88 in SEQ ID No. 2 is reduced by at least 4 amino acid residues.

Embodiment 21

An IL-21 peptide, wherein the length of the region corresponding to amino acid residues 71 to 92 in SEQ ID No. 2 is reduced.

Embodiment 22

A peptide according to embodiment 21, wherein the length of the region corresponding to amino acid residues 71 to 92 in SEQ ID No. 2 is reduced by at least 1 amino acid residue.

Embodiment 23

A peptide according to embodiment 22, wherein the length of the region corresponding to amino acid residues 71 to 92 in SEQ ID No. 2 is reduced by at least 2 amino acid residues.

Embodiment 24

A peptide according to embodiment 23, wherein the length of the region corresponding to amino acid residues 71 to 92 in SEQ ID No. 2 is reduced by at least 3 amino acid residues.

Embodiment 25

A peptide according to embodiment 24, wherein the length of the region corresponding to amino acid residues 71 to 92 in SEQ ID No. 2 is reduced by at least 4 amino acid residues.

Embodiment 26

An IL-21 peptide, wherein the length of the region corresponding to amino acid residues 65 to 92 in SEQ ID No. 2 is reduced.

Embodiment 27

A peptide according to embodiment 26, wherein the length of the region corresponding to amino acid residues 65 to 92 in SEQ ID No. 2 is reduced by at least 1 amino acid residue.

Embodiment 28

A peptide according to embodiment 27, wherein the length of the region corresponding to amino acid residues 65 to 92 in SEQ ID No. 2 is reduced by at least 2 amino acid residues.

Embodiment 29

A peptide according to embodiment 28, wherein the length of the region corresponding to amino acid residues 65 to 92 in SEQ ID No. 2 is reduced by at least 3 amino acid residues.

Embodiment 30

A peptide according to embodiment 29, wherein the length of the region corresponding to amino acid residues 65 to 92 in SEQ ID No. 2 is reduced by at least 4 amino acid residues.

Embodiment 31

An IL-21 peptide, wherein the length of the region corresponding to amino acid residues 77 to 96 in SEQ ID No. 2 is reduced.

Embodiment 32

A peptide according to embodiment 31, wherein the length of the region corresponding to amino acid residues 77 to 96 in SEQ ID No. 2 is reduced by at least 1 amino acid residue.

Embodiment 33

A peptide according to embodiment 32, wherein the length of the region corresponding to amino acid residues 77 to 96 in SEQ ID No. 2 is reduced by at least 2 amino acid residues.

Embodiment 34

A peptide according to embodiment 33, wherein the length of the region corresponding to amino acid residues 77 to 96 in SEQ ID No. 2 is reduced by at least 3 amino acid residues.

Embodiment 35

A peptide according to embodiment 34, wherein the length of the region corresponding to amino acid residues 77 to 96 in SEQ ID No. 2 is reduced by at least 4 amino acid residues.

Embodiment 36

An IL-21 peptide, wherein the length of the region corresponding to amino acid residues 83 to 86 in SEQ ID No. 2 is reduced.

Embodiment 37

A peptide according to embodiment 36, wherein the length of the region corresponding to amino acid residues 83 to 86 in SEQ ID No. 2 is reduced by at least 1 amino acid residue.

Embodiment 38

A peptide according to embodiment 37, wherein the length of the region corresponding to amino acid residues 83 to 86 in SEQ ID No. 2 is reduced by at least 2 amino acid residues.

Embodiment 39

A peptide according to embodiment 38, wherein the length of the region corresponding to amino acid residues 83 to 86 in SEQ ID No. 2 is reduced by at least 3 amino acid residues.

Embodiment 40

An IL-21 peptide, wherein the length of the region corresponding to amino acid residues 83 to 88 in SEQ ID No. 2 is reduced.

Embodiment 41

A peptide according to embodiment 40, wherein the length of the region corresponding to amino acid residues 83 to 88 in SEQ ID No. 2 is reduced by at least 1 amino acid residue.

Embodiment 42

A peptide according to embodiment 41, wherein the length of the region corresponding to amino acid residues 83 to 88 in SEQ ID No. 2 is reduced by at least 2 amino acid residues.

Embodiment 43

A peptide according to embodiment 42, wherein the length of the region corresponding to amino acid residues 83 to 88 in SEQ ID No. 2 is reduced by at least 3 amino acid residues.

Embodiment 44

A peptide according to embodiment 43, wherein the length of the region corresponding to amino acid residues 83 to 88 in SEQ ID No. 2 is reduced by at least 4 amino acid residues.

Embodiment 45

A peptide according to any of embodiments 1 to 44, wherein the length of said region is reduced by the deletion of the necessary amount of amino acid residues in the mentioned region.

Embodiment 46

A peptide according to embodiment 45, wherein said deleted amino acid residues are not all adjacent to each other in the amino acid sequence of the region involved.

Embodiment 47

A peptide according to any of embodiments 1 to 44, wherein the length of said region is reduced by replacing said region with a stretch of amino acid residues, wherein said stretch of amino acid residues is at least 1 amino acid residue shorter than the region it is replacing.

Embodiment 48

An IL-21 peptide according to embodiment 47, wherein said stretch of amino acid residues is at least 2 amino acid residues shorter than the region it is replacing.

Embodiment 49

An IL-21 peptide according to embodiment 48, wherein said stretch of amino acid residues is at least 3 amino acid residues shorter than the region it is replacing.

Embodiment 50

An IL-21 peptide according to embodiment 49, wherein said stretch of amino acid residues is at least 4 amino acid residues shorter than the region it is replacing.

Embodiment 51

An IL-21 peptide according to embodiment 50, wherein said stretch of amino acid residues is at least 5 amino acid residues shorter than the region it is replacing.

Embodiment 52

An IL-21 peptide according to embodiment 51, wherein said stretch of amino acid residues is at least 6 amino acid residues shorter than the region it is replacing.

Embodiment 53

An IL-21 peptide, wherein the region corresponding to amino acid residues 66 to 98 in SEQ ID No. 2 has been replaced by a stretch of amino acid residues, wherein said stretch of amino acid residues is at least 1 amino acid residue shorter than the region it is replacing.

Embodiment 54

An IL-21 peptide according to embodiment 53, wherein said stretch of amino acid residues is at least 2 amino acid residues shorter than the region it is replacing.

Embodiment 55

An IL-21 peptide according to embodiment 54, wherein said stretch of amino acid residues is at least 3 amino acid residues shorter than the region it is replacing.

Embodiment 56

An IL-21 peptide according to embodiment 55, wherein said stretch of amino acid residues is at least 4 amino acid residues shorter than the region it is replacing.

Embodiment 57

An IL-21 peptide according to embodiment 56, wherein said stretch of amino acid residues is at least 5 amino acid residues shorter than the region it is replacing.

Embodiment 58

An IL-21 peptide according to embodiment 57, wherein said stretch of amino acid residues is at least 6 amino acid residues shorter than the region it is replacing.

Embodiment 59

An IL-21 peptide according to any of embodiments 47 to 58, wherein said stretch of amino acid residues is of IL-21 origin.

Embodiment 60

An IL-21 peptide according to embodiment 59, wherein said stretch of amino acid residues originates from within the region corresponding to amino acid residues 66 to 98 in SEQ ID No. 2.

Embodiment 61

An IL-21 peptide according to embodiment 59 or 60, wherein said stretch of amino acid residues comprises at least one non-conservative substitution of an amino acid residue present in the region corresponding to amino acid residues 66 to 98 in SEQ ID No. 2.

Embodiment 62

An IL-21 peptide according to any of embodiments 59 to 61, wherein said stretch of amino acid residues comprises a deletion of amino acids 77 to 92 of SEQ ID No. 2.

Embodiment 63

An IL-21 peptide according to any of embodiments 59 to 61, wherein said stretch of amino acid residues comprises a deletion of amino acids 83 to 90 of SEQ ID No. 2.

Embodiment 64

An IL-21 peptide according to any of embodiments 59 to 61, wherein said stretch of amino acid residues comprises a deletion of amino acids 82 to 88 of SEQ ID No. 2.

Embodiment 65

An IL-21 peptide according to any of embodiments 59 to 61, wherein said stretch of amino acid residues comprises a deletion of amino acids 71 to 92 of SEQ ID No. 2.

Embodiment 66

An IL-21 peptide according to any of embodiments 59 to 61, wherein said stretch of amino acid residues comprises a deletion of amino acids 65 to 92 of SEQ ID No. 2.

Embodiment 67

An IL-21 peptide according to any of embodiments 59 to 61, wherein said stretch of amino acid residues comprises a deletion of amino acids 77 to 96 of SEQ ID No. 2.

Embodiment 68

An IL-21 peptide according to any of embodiments 59 to 61, wherein said stretch of amino acid residues comprises a deletion of amino acids 83 to 86 of SEQ ID No. 2.

Embodiment 69

An IL-21 peptide according to any of embodiments 59 to 61, wherein said stretch of amino acid residues comprises a deletion of amino acids 83 to 88 of SEQ ID No. 2.

Embodiment 70

An IL-21 peptide according to any of embodiments 59 to 61, wherein said stretch of amino acid residues comprises one or more non-adjacent deletions in the region corresponding to amino acid residues 66 to 98 in SEQ ID No. 2.

Embodiment 71

An IL-21 peptide according to embodiment 59 or 60, wherein said stretch of amino acid residues comprises at least one non-conservative substitution of an amino acid residue present in the region corresponding to amino acid residues 77 to 92 in SEQ ID No. 2.

Embodiment 72

An IL-21 peptide according to embodiment 71, wherein said stretch of amino acid residues comprises a deletion of amino acids 83 to 90 of SEQ ID No. 2.

Embodiment 73

An IL-21 peptide according to embodiment 71, wherein said stretch of amino acid residues comprises a deletion of amino acids 82 to 88 of SEQ ID No. 2.

Embodiment 74

An IL-21 peptide according to embodiment 71, wherein said stretch of amino acid residues comprises a deletion of amino acids 83 to 86 of SEQ ID No. 2.

Embodiment 75

An IL-21 peptide according to embodiment 71, wherein said stretch of amino acid residues comprises a deletion of amino acids 83 to 88 of SEQ ID No. 2.

Embodiment 76

An IL-21 peptide according to embodiment 71, wherein said stretch of amino acid residues comprises one or more non-adjacent deletions in the region corresponding to amino acid residues 77 to 92 in SEQ ID No. 2.

Embodiment 77

An IL-21 peptide according to any of embodiments 47 to 58, wherein said stretch of amino acid residues is of non-IL-21 origin.

Embodiment 78

An IL-21 peptide according to any of embodiments 1 to 77 with the provisio that the peptide does not have the sequence of SEQ ID No. 3, 4, 5 or 6 or the sequence of a peptide having the sequence of SEQ ID No. 3, 4, 5 or 6 with an additional N-terminal methionine.

Embodiment 79

An IL-21 peptide according to any of embodiments 1 to 77 with the provisio that the peptide does not have the sequence of SEQ ID No. 7, 8, 9 or 10 or the sequence of a peptide having the sequence of SEQ ID No. 7, 8, 9 or 10 with an additional N-terminal methionine.

Embodiment 80

An IL-21 peptide according to any of embodiments 1 to 77 with the provisio that the peptide does not have a substitution mutation in the position corresponding to Asn-68 in SEQ ID No. 2.

Embodiment 81

An IL-21 peptide according to any of embodiments 1 to 77 with the provisio that the amino acid residue in the position corresponding to Asn-68 in SEQ ID No. 2 is not a Gln.

Embodiment 82

An IL-21 peptide according to any of embodiments 1 to 77 with the provisio that the IL-21 peptide does not have a substitution mutation in the position corresponding to Ser-80 in SEQ ID No. 2.

Embodiment 83

An IL-21 peptide according to any of embodiments 1 to 77 with the provisio that the amino acid residue in the position corresponding to Ser-80 in SEQ ID No. 2 is not a Thr.

Embodiment 84

An IL-21 peptide according to any of embodiments 1 to 77 with the provisio that the IL-21 peptide does not have a substitution mutation in the position corresponding to Gln-87 in SEQ ID No. 2.

Embodiment 85

An IL-21 peptide according to any of embodiments 1 to 77 with the provisio that the amino acid residue in the position corresponding to Gln-87 in SEQ ID No. 2 is not a Asn.

Embodiment 86

An IL-21 peptide according to any of embodiments 1 to 77 with the provisio that the IL-21 peptide does not have substitution mutation in the position corresponding to Asn-68, in the position corresponding to Ser-80 in SEQ ID No. 2 and in the position corresponding to Gln-87 in SEQ ID No. 2.

Embodiment 87

An IL-21 peptide according to any of embodiments 1 to 77 with the provisio that the amino acid residue in the position corresponding to Asn-68 in SEQ ID No. 2 is not a Gln, the amino acid residue in the position corresponding to Ser-80 in SEQ ID No. 2 is not a Thr and the amino acid residue in the position corresponding to Gln-87 in SEQ ID No. 2 is not a Asn.

Embodiment 88

A peptide according to any of embodiments 1 to 87, wherein the potency of the peptide is at least substantially similar to the potency of wildtype IL-21 in one or more of the assays as described in the Examples.

Embodiment 89

A peptide according to any of embodiments 1 to 87, wherein the potency of the peptide is substantially higher than the potency of wildtype IL-21 in one or more of the assays as described in the Examples.

Embodiment 90

A peptide according to any of embodiments 1 to 87, wherein the potency of the peptide is at least 2 fold higher than the potency of wildtype IL-21 in one or more of the assays as described in the Examples.

Embodiment 91

A peptide according to any of embodiments 1 to 87, wherein the potency of the peptide is at least 5 fold higher than the potency of wildtype IL-21 in one or more of the assays as described in the Examples.

Embodiment 92

A peptide according to any of embodiments 1 to 87, wherein the potency of the peptide is about 10 fold higher than the potency of wildtype IL-21 in one or more of the assays as described in the Examples.

Embodiment 93

A peptide according to any of embodiments 1 to 92 for use in therapy.

Embodiment 94

A peptide according to any of embodiments 1 to 92, wherein the peptide is an agonist of the IL-21 receptor for use in the treatment of cancer.

Embodiment 95

A peptide according to any of embodiments 1 to 92, wherein the peptide is an agonist of the IL-21 receptor for the treatment of cancer.

Embodiment 96

A peptide according to embodiment 94 or embodiment 95, wherein the cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

Embodiment 97

A peptide according to embodiment 96, wherein the cancer is malignant melanoma.

Embodiment 98

A pharmaceutical composition comprising a peptide according to any of embodiments 1 to 92.

Embodiment 99

The composition according to embodiment 98, wherein the peptide is an agonist of the IL-21 receptor, and said composition further comprises a cancer agent.

Embodiment 100

A method for the treatment of cancer, the treatment comprising the administration of an effective amount of a peptide according to any of embodiments 1 to 92, wherein said peptide is an agonist of the IL-21 receptor, optionally in combination with a cancer agent, to a patient in need thereof.

Embodiment 101

A method according to embodiment 100, wherein the cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

Embodiment 102

A method according to embodiment 101, wherein the cancer is malignant melanoma.

Embodiment 103

Use of a peptide according to any of embodiments 1 to 92, wherein the peptide is an agonist of the IL-21 receptor, in the manufacture of a medicament for the treatment of cancer.

Embodiment 104

A use according to embodiment 103, wherein the cancer is selected from non-metastatic and metastatic neoplastic disorders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

Embodiment 105

A use according to embodiment 104, wherein the cancer is malignant melanoma.

Embodiment 106

A use according to embodiment, wherein the cancer is selected from non-metastatic and metastatic neoplastic dis-

Embodiment 107

A use according to embodiment 106, wherein the cancer is malignant melanoma.

Embodiment 108

A peptide according to any of embodiments 1 to 92, wherein the peptide is an antagonist of the IL-21 receptor for use in the treatment of inflammatory diseases, for instance autoimmune diseases, such as SLE, RA and IBD.

Embodiment 109

A method for the treatment of inflammatory diseases, such as autoimmune diseases, for instance SLE, RA and IBD, the treatment comprising the administration of an effective amount of a peptide according to any of embodiments 1 to 92, wherein said peptide is an antagonist of the IL-21 receptor, to a patient in need thereof.

Embodiment 110

Use of a peptide according to any of embodiments 1 to 92, wherein said peptide is an antagonist of the IL-21 receptor, in the manufacture of a medicament for the treatment of inflammatory diseases, such as autoimmune diseases, for instance SLE, RA and IBD.

Embodiment 111

A nucleic acid construct encoding a peptide according to any of embodiments 1 to 92.

Embodiment 112

A vector comprising the nucleic acid construct according to embodiment 111.

Embodiment 113

A host comprising the nucleic acid construct of embodiment 111, or the vector of embodiment 112.

Embodiment 114

Antibodies against a peptide according to any of embodiments 1 to 92.

Embodiment 115

An antibody that specifically binds a peptide according to any of embodiments 1 to 92.

Embodiment 116

An antibody according to embodiment 112, which does not bind to wild-type IL-21.

orders such as malignant melanoma, non-melanoma skin cancers, renal cell carcinoma, cancer of the head and neck, cancer of the endocrine system, ovarian cancer, small-cell lung cancer, non small-cell lung cancer, breast cancer, esophageal cancer, upper gastro-intestinal cancer, colorectal cancer, liver and bile duct cancer, pancreatic cancer, prostate cancer, bladder cancer, testicular cancer, cervical cancer, endometrial cancer, sarcomas of bones and soft tissue, cancer of the central nervous system, lymphoma, leukaemia, and cancer of unknown primary origin.

EXAMPLES

Binding of IL-21 Peptide to IL-21 Receptor Using Baf-Cells hIL-21 wild type and mutant proteins were analyzed using in a cellular activity assay using a stat-regulated luciferase reporter system.

The assay employs the murine Baf3 cell line, which has been stably transfected to express the human IL-21R and a Stat-linked luciferase reporter construct. The Baf3 cells expresses endogenously the gamma C 'common chain' which constitutes an essential component of the signalling IL-21 receptor complex. The Baf3/hIL-21R reporter cell line was starved in IL-3 free medium for 6 hours prior to stimulation. A dosis-response analysis was subsequently carried out using stimulation of the cells for 24 hours.

The binding of several IL-21 peptides to the IL-21 receptor is shown in FIGS. 1, 2, and 3.

Binding of IL-21 Peptide to IL-21 Receptor

The cDNAs encoding the IL-21 variants are analyzed by transient expression followed by activity analysis in a stat-regulated reporter system.

The cDNAs are transfected into HEK293 FreeStyle cells (Stengaard-Pedersen et al. N. Engl. J. Med. 349, 554 (2003); Invitrogen). Supernatants are collected from serum-free medium at 48 hours post transfection and analyzed in a cellular bioassay. The assay employs the murine Baf3 cell line, stably transfected to express the human IL-21R and a Stat-linked luciferase reporter construct. The Baf3 cells expresses endogenously the γc component of the active IL-21 receptor complex. The Baf3/hIL-21R reporter cell line is starved in IL-3 free medium for 18 hours prior to stimulation. A dosis-response analysis is carried out using raw supernatant from the HEK293-FS transfectants. Duration of the stimulation is four hours.

Pharmacological Methods

The following in vitro method is used to investigate enhancement of ADCC.

Target cells expressing the target antigen are incubated with the antibody against the target antigen and peripheral blood mononuclear cells, NK cells, neutrophils, macrophages, monocytes or DC as effector cells. Effector cells may be pre-incubated for 1 to 10 days with IL-21, or IL-21 may be added to the culture containing both effector and target cells. Other compounds that can enhance ADCC might be included in the culture or preincubation culture. Efficiency of ADCC will be measured as specific $^{51}$Cr release from the target cells or as LDH activity as described previously (Golay et al., *Haematologica* 88:1002-1012, 2003 or Liu et al., *Cancer Immun* 2:13, 2002 or Watanabe et al., *Breast Cancer Res Treat* 53:199-207, 1999).

Determination of ADCC using a flow cytometry based assay as described previously (Flieger et. al., *J Immunother* 23:480-486, 2000 or Flieger et al., *J Immunol Methods* 180: 1-13, 1995 or Flieger et al., *Hybridoma* 18:63-68, 1999).

Determination of ADCP through two-color fluorescence assay as described in Watanabe et al., *Breast Cancer Res Treat* 53:199-207, 1999 or Akewanlop et al., *Cancer Res* 61:4061-4065, 2001.

An in vivo method for determining the enhancement of ADCC is outlined below:

Leukaemia cells or transformed cells are injected i.v., i.p. or s.c. in syngeneic animals followed by treatment with the therapeutic antibody recognising an antigen expressed by the leukaemia cells or transformed cells, with or without IL-21 therapy. Endpoints are tumor burden and survival. The involvement of ADCC may be confirmed by the use of FcγRI blocking antibodies or by the use of FcγRI-deficient mice.

An in vivo method to investigate enhancement of ADCC towards target cells of human origin is described previously in Zhang et al., *Blood* 102:284-288, 2003 or Flavell et al. *Cancer Res* 58:5787-5794, 1998. According to these models human leukaemia cells or transformed cells are injected i.v., i.p. or s.c. in SCID mice followed by treatment with the therapeutic antibody recognising an antigen expressed by the leukaemia cells or transformed cells, with or without IL-21 therapy.

Tumor cell lines, e.g. Lewis Lung Carcinoma (LLC) cells or B16-F10 melanoma cells or renal renal cell carcinoma cells or 4T1 breast carcinoma cells are implanted s.c. in syngeneic mice. When the tumors become palpable, the mice are treated with IL-21 in combination with other anti-cancer agents as described in this application. The methodology is described in Palumbo et al., Cancer Res. 62, 6966-6972 (2002); Bove et al., Biochem Biophys Res Commun 291, 1001-1005 (2002); Wigginton et al., J Immunol 169, 4467-4474 (2002).

Tumor cell lines, e.g. Lewis Lung Carcinoma (LLC) cells or B16-F10 melanoma cells are implanted s.c. in syngeneic mice. The primary tumor is removed after 1-4 weeks, and the mice are treated with IL-21 in combination with other anti-cancer agents as described in this application. The methodology is described in Palumbo et al., Cancer Res. 62, 6966-6972 (2002).

Tumor cell lines, e.g. Lewis Lung Carcinoma (LLC) cells or B16-F10 melanoma cells or renca renal cell carcinoma cells are injected i.v. in syngeneic mice and the mice are treated with IL-21 in combination with other anti-cancer agents as described in this application. The methodology is described in Amirkhosravi et al., Thromb. Haemost. 87, 930-936 (2002); Hosaka et al., Cancer Lett 161, 231-240 (2000); Maini et al., In vivo 17, 119-123 (2003).

Renal renal cell carcinoma cells are injected intra-renally in one kidney in syngeneic mice. The primary tumor is removed after 1-4 weeks, and the mice are treated with IL-21 in combination with other anti-cancer agents as described in this application. The methodology is described in Murphy et al., J Immunol 170, 2727-2733 (2003).

The invention claimed is:

1. An isolated variant IL-21 peptide comprising an amino acid sequence, which varies from SEQ ID NO:2 in that amino acid residues 83-88 in SEQ ID NO:2 are deleted, and amino acid residues at positions 77-79, 81 and 91 in SEQ ID NO: 2 are replaced by non-conservative amino acid residues, and wherein amino acid residues at positions 82, 89 and 90 are either deleted or replaced by non-conservative amino acid residues, wherein the variant binds to the human IL-21 receptor.

2. The variant IL-21 peptide of claim 1, wherein amino acid residues 83-90 in SEQ ID NO: 2 are deleted.

3. The variant IL-21 peptide of claim 1, wherein amino acid residues 82-88 in SEQ ID NO: 2 are deleted.

4. The variant IL-21 peptide of claim 1, wherein the amino acid residues at positions 75, 77-79, 81, 82, 89, 90, and 91 in SEQ ID NO: 2 are replaced by non-conservative substitutions.

5. The variant IL-21 peptide of claim 1, further comprising an N-terminal Met.

6. A pharmaceutical composition comprising an IL-21 peptide of claim 1.

* * * * *